United States Patent [19]

Di Marchi

[11] 4,451,396

[45] May 29, 1984

[54] PROCESS FOR INHIBITING UNDESIRED THIOL REACTIONS DURING CYANOGEN BROMIDE CLEAVAGE OF PEPTIDES

[75] Inventor: Richard D. Di Marchi, Carmel, Ind.

[73] Assignee: Eli Lilly and Company, Indianapolis, Ind.

[21] Appl. No.: 519,169

[22] Filed: Aug. 1, 1983

[51] Int. Cl.³ .................... C07G 7/00; C07C 103/52; A61K 37/26
[52] U.S. Cl. .................... 260/112 R; 260/112.5 R; 260/112.7
[58] Field of Search .................... 260/112 R, 112.5 R, 260/112.7

[56] References Cited

U.S. PATENT DOCUMENTS 3,883,500  5/1975  Geiger et al. .................... 260/112.7

OTHER PUBLICATIONS

Ho et al., *Synthetic Communications 3*, 317–320 (1973).
Abe et al., *J. Org. Chem. 39*, 253–255 (1974).
Sekita et al., *Keio J. Med. 24*, 203–210 (1975).

*Primary Examiner*—Howard E. Schain
*Attorney, Agent, or Firm*—William C. Martens, Jr.; Arthur R. Whale

[57] ABSTRACT

The discovery of this invention is a process for inhibiting undesired irreversible thiol reactions of thiol-containing peptides while preforming desirable thiol intermediates during methionyl cleavage of said peptides using CNBr by carrying out said cleavage in the presence of thiosulfate ion.

7 Claims, No Drawings

PROCESS FOR INHIBITING UNDESIRED THIOL REACTIONS DURING CYANOGEN BROMIDE CLEAVAGE OF PEPTIDES

BACKGROUND OF THE INVENTION

The advent of recombinant DNA methodology carried the need for development of a number of process parameters for product production, recovery, and purification. Customarily, products produced by recombinant DNA processes are initially obtained as "fused gene products", i.e., amino acid sequences containing a leading sequence and/or following sequence joined to the amino acid sequence of the desired product. It has been essential, therefore, to devise methodology for cleaving the desired peptide from any extraneous peptide. One hitherto recognized chemical method has been extensively applied. It involves the use of cyanogen bromide (CNBr) to induce cleavage at the peptide carboxy-terminal of any internal methionyl residue. Precise location of a methionyl residue at the juncture of the amino-terminal of the desired product and the extraneous peptide coupled with the absence within the desired product of available methionyl residues makes CNBr cleavage a potentially highly useful method for product preparation in recombinant DNA processes.

However, the use of CNBr to effect specific cleavage is not without its drawbacks. One particular drawback is evident in the processing of peptides having thiol-containing amino acid residues. Cyanogen bromide is recognized to promote conversion of thiols to disulfides thereby leading, during CNBr cleavage, to the production of unwanted by-products. Ho et al., *Synthetic Communications* 3, 317–320 (1973), describe the reaction of CNBr with alkyl and aryl sodium thiolates to produce the corresponding disulfides. Abe et al., *J. Org. Chem.* 39, 253–255 (1974) describe the reaction of homocystine with 2-mercaptoethanol to produce homocysteine and the mixed disulfide of homocysteine and 2-mercaptoethanol. The reaction is conducted both in the presence and absence of CNBr. The amount of mixed disulfide is greatly increased in the presence of CNBr with corresponding reduction of the amount of homocysteine.

From another perspective, Sekita et al., *Keio J. Med.* 24, 203–210 (1975), describe CNBr cleavage of urease and phosphorylase b. Their studies suggest that the cleavage can be increased by addition of 2-mercaptoethanol; however, they postulate no definitive basis for this effect. They further report that this effect is not achieved using either dithiothreitol or thiodiglycol.

It now has been discovered that the undesired disulfide interchange and irreversible cysteine modification mediated by CNBr on fermentation solids obtained from recombinant DNA processes can be diminished or eliminated by addition of a small amount of thiosulfate ion prior to CNBr cleavage. Routinely, the production of thiol-containing peptides by recombinant DNA methods involves original features of the recombinant organisms, recovery of fermentation solids, cleavage of the fused gene product using CNBr, and sulfitolysis of the cleaved product to obtain an S-sulfonated peptide ready for combination with an independently derived S-sulfonate peptide or for folding upon itself to produce the desired disulfide containing product. It has been observed through subsequent sulfitolysis of the product mixture that the action of CNBr on thiol-containing materials leads to the production of quantities of irreversibly modified derivatives which complicate chromatographic purification procedures and decrease yield. Thus, both product loss and chromatographically similar contaminants result. Both of these disadvantages, it has been discovered, are significantly diminished or eliminated by the presence of thiosulfate ion.

Moreover, it has been discovered that the use of thiosulfate ion during CNBr cleavage of a thiol-containing peptide has an added benefit. It generates an intermediate, presumably the sulfenyl S-sulfonate, which facilitates the customarily subsequent sulfitolysis reaction. Sulfitolysis traditionally involves treatment of the thiol peptide with sodium sulfate in the presence of an oxidizing agent, of which sodium tetrathionate has proven most successful. The intermediate produced during CNBr cleavage in the presence of thiosulfate ion is readily converted to the sulfitolyzed product by treatment with sodium sulfite in the absence of the costly sodium tetrathionate reagent.

It is thus to a process as aforedescribed for achieving CNBr cleavage that this invention is directed.

SUMMARY OF THE INVENTION

Thus, this invention is directed to a process for inhibiting undesired thiol reactions of thiol-containing peptides during methionyl cleavage of said peptides using CNBr, which comprises carrying out said cleavage in the presence of thiosulfate ion.

DETAILED DESCRIPTION OF THE INVENTION

The process of this invention involves the interaction of a peptide, CNBr, and thiosulfate ion. The desired peptide must contain at least one methionine residue subject to attack and cleavage by cyanogen bromide and a minimum of one thiol-containing amino acid. Examples of peptides meeting the above criteria are growth hormones, proinsulins, insulin A-chain, and insulin B-chain.

The cleavage reaction in accordance with the process of this invention is carried out in the presence of an aqueous-acid solvent. Typical acids which may be used are trifluoroacetic acid, acetic acid, hydrochloric acid, sulfuric acid, phosphoric acid, formic acid, and the like. Formic acid is highly preferred. Moreover, although other non-aqueous, non-acidic solvents may be included in the solvent mixture, it is highly preferred that the ratio of acid to water be carefully controlled. Optimally, whether the solvent mixture includes non-acidic, non-aqueous components or not, the amount of acid present will be in molar excess relative to the water. In particular, in the case of formic acid, the preferred acid-aqueous mixture is 67.5% formic acid by volume.

Cyanogen bromide is incorporated into the mixture in an amount sufficient at least to account on a mole per mole basis for each methionine present in the peptide starting material. A large excess of CNBr can be employed without detriment; generally, therefore, the CNBr will be present in approximately a 6–10 fold molar ratio relative to the peptide methionyl residues. Moreover, if what normally would be an excess of CNBr is not used, it is necessary, in the process of this invention, to add an additional amount of CNBr sufficient to account on a mole-mole basis for the amount of thiosulfate ion incorporated into the mixture. In summary, however, the required amount of CNBr can be achieved by ensuring the presence of a large excess relative to the sum of methionyl residue and thiosulfate.

The essence of the process of this invention resides in the addition of thiosulfate ion. Typically, thiosulate will be incorporated in the form of its inorganic salt, generally an alkali metal salt, such as sodium thiosulfate, potassium thiosulfate, and the like. The salt of choice is sodium thiosulfate.

The amount of thiosulfate used is directly dependent upon the amount of thiol present in the mixture. At least one mole of thiosulfate must be used per each mole of thiol, and, should there be contaminating nucleophiles in the reaction mixture, sufficient thiosulfate to account for and neutralize them. A large excess of thiosulfate, therefore, can be and generally is employed, for example, up to about 10-fold, based upon thiol content, without detriment. It must be noted, however, that, although there is virtually no upper limit on the amount of thiosulfate which can be used in this process, thiosulfate consumes cyanogen bromide and, therefore, necessitates the presence of CNBr in an amount above that required under normal conditions. Preferably, therefore, the amount of thiosulfate will be controlled to minimize needless consumption of NCBr.

The cleavage reaction in accordance with the process of this invention is carried out at a temperature of from about 15° C. to the boiling point of CNBr (about 35° C.). Preferably, the reaction is conducted at a temperature of from about 15° C. to about 30° C., and, most preferably, from about 20° C. to about 25° C.

The reaction is carried out for a period sufficient to complete methionyl cleavage, generally up to about 12 hours. Normally, the reaction is complete after about 6 hours.

Upon completion of methionyl cleavage, the mixture generally is evaporated to near dryness under reduced pressure at about 25° C. The residue is dissolved in water at about twice the original concentration, and the solution is lyophilized. Sulfitolysis of the crude lyophilized solids is performed generally at 50 gm. of product per liter of 7 M urea in the presence 0.1 M sodium sulfite, 1 mM cysteine, and 0.1 M ethylene diamine at pH 8.5, 22° C. for 8 hours.

As is apparent, the process of this invention is highly advantageous for minimizing irreversible side reactions and for generating peptide intermediates particularly suited for ready conversion into sulfitolysis products which in turn can be used to produce the desired disulfide final product.

The following examples are provided to illustrate the process of this invention. They are not intended to be limiting upon the broad scope thereof.

EXAMPLE 1

Production of Insulin A-Chain Cleaved Fused Gene Product

To 500 mg of A-chain lyophilized fermentation solids was added 10 ml of 67.5% formic acid (v/v). After 15 minutes of stirring, 15 mg (3% wt/wt of crude fermentation solids) of sodium thiosulfate pentahydrate was added. Following solubilization of the sodium thiosulfate, cyanogen bromide was added to a concentration of 0.05 M (53 mg). The reaction was complete after 12 hours at 22° C. The sample was evaporated in vacuo, solubilized to twice its original concentration in water, and lyophilized.

EXAMPLE 2

Production of Insulin B-Chain Cleaved Fused Gene Product

To 900 mg of B-chain lyophilized fermentation solids was added 10 ml of 67.5% formic acid (v/v). After 15 minutes of stirring, 27 mg (3% wt/wt of crude fermentation solids) of sodium thiosulfate pentahydrate was added. Following solubilization of the sodium thiosulfate, cyanogen bromide was added to a concentration of 0.10 M (106 mg). The reaction was complete after 12 hours at 22° C. The sample was evaporated in vacuo, solubilized to twice its original concentration in water, and lyophilized.

EXAMPLE 3

Production of Proinsulin Cleaved Fused Gene Product

To one gram of proinsulin lyophilized fermentation solids was added 10 ml of 67.5% formic acid (v/v). After 15 minutes of stirring, 30 mg (3% wt/wt of crude fermentation solids) of sodium thiosulfate pentahydrate was added. Following solubilization of the sodium thiosulfate, cyanogen bromide was added to a concentration of 0.10 M (106 mg). The reaction was complete after 12 hours at 22° C. The sample was evaporated in vacuo, solubilized to twice it original concentration in water, and lyophilized.

EXAMPLE 4

Sulfitolysis of Cleaved Fused Gene Products

The cleaved fused gene products obtained from Examples 1–3 were subjectd to sulfitolysis using the following procedure:

To 500 mg. of CNBr cleaved fermentation solids dissolved in 10 ml. of 0.1 M ethylene diamine/7 M deionized urea at pH 8.5 was added sodium sulfate to 0.1 M and cysteine to 1 mM concentrations. Following dissolution, the reaction was complete after 8 hours at 22° C.

Sulfitolysis of product obtained as in the aforedescribed Examples 1–3 was compared with that obtained from CNBr cleavage carried out in the absence of sodium thiosulfate. As the Table following depicts, the presence of sodium thiosulfate during CNBr cleavage substantially increases the amount of product available for sulfitolysis and the quantity of sulfitolyzed product per unit solids.

TABLE

| Sulfitolysis starting material | $Na_2SSO_3$ in CNBr Cleavage | $Na_2S_4O_6$ in Sulfitolysis | Product Yield, mg./g. solids at Given Reaction Time, Hours | | |
|---|---|---|---|---|---|
| | | | 2 | 6 | 24 |
| Insulin A-chain | No | No | 1.8 | 5.0 | — |
| Insulin A-chain | Yes | No | 7.1 | 6.8 | — |
| Insulin A-chain | No | Yes | 6.5 | — | — |
| Insulin B-chain | No | No | 8.4 | 9.6 | — |
| Insulin B-chain | Yes | No | 11.5 | 12.4 | — |
| Insulin B-chain | No | Yes | 9.4 | — | — |
| Proinsulin | No | No | 0.8 | 3.0 | 4.1 |
| Proinsulin | Yes | No | 7.8 | 9.4 | 9.1 |
| Proinsulin | No | Yes | 5.4 | — | — |

I claim:

1. A process for inhibiting undesired thiol reactions of thiol-containing peptides during methionyl cleavage of said peptides using CNBr, which comprises carrying out said cleavage in the presence of thiosulfate ion.

2. Process of claim 1, in which the thiosulfate ion is incorporated in the cleavage reaction mixture as its alkali metal salt.

3. Process of claim 2, in which the alkali metal salt is sodium thiosulfate.

4. Process of claim 3, in which the thiosulfate ion is added to the reaction mixture in an amount sufficient to represent at least one mole thiosulfate per mole of thiol.

5. Process of claim 4, in which the methionyl cleavage is carried out in the presence of an aqueous-acid solvent.

6. Process of claim 5, in which the acid is formic acid.

7. Process of claim 6, in which the mixture of formic acid and water comprises, by volume, 67.5% formic acid.

* * * * *

UNITED STATES PATENT AND TRADEMARK OFFICE
CERTIFICATE OF CORRECTION

PATENT NO. : 4,451,396
DATED : May 29, 1984
INVENTOR(S) : Richard D. DiMarchi

It is certified that error appears in the above—identified patent and that said Letters Patent is hereby corrected as shown below:

Column 2, line 12, "..peptide with sodium sulfate in the presence of an..." should read --..peptide with sodium sulfite in the presence of an...--.

Column 4, line 38, "..ionized urea at pH 8.5 was added sodium sulfate to 0.1..." should read --..ionized urea at pH 8.5 was added sodium sulfite to 0.1...--.

Signed and Sealed this

Sixth Day of August 1985

[SEAL]

Attest:

DONALD J. QUIGG

Attesting Officer     Acting Commissioner of Patents and Trademarks